(12) United States Patent
Morgan et al.

(10) Patent No.: US 7,673,783 B2
(45) Date of Patent: Mar. 9, 2010

(54) SURGICAL STAPLING INSTRUMENTS STRUCTURED FOR DELIVERY OF MEDICAL AGENTS

(75) Inventors: Jerome R. Morgan, Cincinnati, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 110 days.

(21) Appl. No.: 11/267,811

(22) Filed: Nov. 4, 2005

(65) Prior Publication Data

US 2007/0102453 A1 May 10, 2007

(51) Int. Cl.
*A61B 17/072* (2006.01)
(52) U.S. Cl. .................. 227/180.1; 227/175.1; 227/19
(58) Field of Classification Search ... 227/175.1–182.1, 227/19
See application file for complete search history.

(56) References Cited

U.S. PATENT DOCUMENTS

| | | | |
|---|---|---|---|
| 2,037,727 A | 4/1936 | Chapelle | |
| 2,853,074 A | 9/1958 | Olson | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 3,894,174 A | 7/1975 | Cartun | |
| 3,940,844 A | 3/1976 | Colby et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,475,679 A | 10/1984 | Fleury, Jr. | |
| 4,500,024 A | 2/1985 | DiGiovanni et al. | |

(Continued)

FOREIGN PATENT DOCUMENTS

CA    2458946 A1    3/2003

(Continued)

OTHER PUBLICATIONS

U.S. Nonprovisional Patent Application for Surgical Stapling Instrument Having an Electroactive Polymer Actuated Medical Substance Dispenser, Inventors: Frederick E. Shelton IV, Joseph C. Hueil, Jerry R. Morgan.

(Continued)

*Primary Examiner*—Rinaldi I. Rada
*Assistant Examiner*—Lindsay Low

(57) ABSTRACT

A medical agent dispensing system can be provided that may be structured for use with a surgical severing/stapling instrument that is designed for severing and stapling tissue. The dispensing system may include at least one storage reservoir structured for storing at least a component of a medical agent; a gear pump casing in communication with the storage reservoir; a screw pump auger positioned within the gear pump casing capable of rotational manipulation to move the medical agent through the gear pump casing; and, at least one agent tube in communication with the gear pump casing. The agent tube may be structured for communication with a least one agent port formed in a staple cartridge of the surgical instrument for dispensing the medical agent therethrough.

20 Claims, 7 Drawing Sheets

U.S. PATENT DOCUMENTS

| | | | |
|---|---|---|---|
| 4,506,671 A | 3/1985 | Green | |
| 4,520,817 A | 6/1985 | Green | |
| 4,522,327 A | 6/1985 | Korthoff et al. | |
| 4,526,174 A | 7/1985 | Froehlich | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,606,343 A | 8/1986 | Conta et al. | |
| 4,610,383 A | 9/1986 | Rothfuss et al. | |
| 4,619,262 A | 10/1986 | Taylor | |
| 4,629,107 A | 12/1986 | Fedotov et al. | |
| 4,664,305 A | 5/1987 | Blake, III et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,728,020 A | 3/1988 | Green et al. | |
| 4,754,909 A | 7/1988 | Barker et al. | |
| 4,767,044 A | 8/1988 | Green | |
| 4,809,695 A | 3/1989 | Gwathmey et al. | |
| 4,817,847 A | 4/1989 | Redtenbacher et al. | |
| 4,821,939 A | 4/1989 | Green | |
| 4,869,414 A | 9/1989 | Green et al. | |
| 4,869,415 A | 9/1989 | Fox | |
| 4,892,244 A | 1/1990 | Fox et al. | |
| 4,941,623 A | 7/1990 | Pruitt | |
| 4,944,443 A | 7/1990 | Oddsen et al. | |
| 4,955,959 A | 9/1990 | Tompkins et al. | |
| 5,027,834 A | 7/1991 | Pruitt | |
| 5,031,814 A | 7/1991 | Tompkins et al. | |
| 5,040,715 A | 8/1991 | Green et al. | |
| 5,065,929 A | 11/1991 | Schulze et al. | |
| 5,080,556 A | 1/1992 | Carreno | |
| 5,089,606 A * | 2/1992 | Cole et al. | 536/54 |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,137,198 A | 8/1992 | Nobis et al. | |
| 5,156,315 A | 10/1992 | Green et al. | |
| 5,211,649 A | 5/1993 | Kohler et al. | |
| 5,221,036 A | 6/1993 | Takase | |
| 5,246,156 A | 9/1993 | Rothfuss et al. | |
| 5,253,793 A | 10/1993 | Green et al. | |
| RE34,519 E | 1/1994 | Fox et al. | |
| 5,275,323 A | 1/1994 | Schulze et al. | |
| 5,307,976 A | 5/1994 | Olson et al. | |
| 5,313,967 A * | 5/1994 | Lieber et al. | 600/585 |
| 5,318,221 A | 6/1994 | Green et al. | |
| 5,350,400 A | 9/1994 | Esposito et al. | |
| 5,379,933 A | 1/1995 | Green et al. | |
| 5,383,880 A | 1/1995 | Hooven | |
| 5,395,033 A | 3/1995 | Byrne et al. | |
| 5,397,046 A | 3/1995 | Savage et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,433,721 A | 7/1995 | Hooven et al. | |
| 5,445,304 A | 8/1995 | Plyley et al. | |
| 5,456,401 A | 10/1995 | Green et al. | |
| 5,462,215 A | 10/1995 | Viola et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,480,089 A | 1/1996 | Blewett | |
| 5,482,197 A | 1/1996 | Green et al. | |
| 5,484,095 A | 1/1996 | Green et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,547,117 A | 8/1996 | Hamblin et al. | |
| 5,553,765 A | 9/1996 | Knodel et al. | |
| 5,554,169 A | 9/1996 | Green et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,564,615 A | 10/1996 | Bishop et al. | |
| 5,577,654 A | 11/1996 | Bishop | |
| 5,579,978 A | 12/1996 | Green et al. | |
| 5,580,067 A | 12/1996 | Hamblin et al. | |
| 5,583,114 A * | 12/1996 | Barrows et al. | 514/21 |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,591,187 A * | 1/1997 | Dekel | 606/180 |
| 5,597,107 A | 1/1997 | Knodel et al. | |
| 5,601,224 A | 2/1997 | Bishop et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,685,474 A | 11/1997 | Seeber | |
| 5,688,270 A | 11/1997 | Yates et al. | |
| 5,690,269 A | 11/1997 | Bolanos et al. | |
| 5,692,668 A | 12/1997 | Schulze et al. | |

| | | | |
|---|---|---|---|
| 5,697,543 A | 12/1997 | Burdorff | |
| 5,702,408 A | 12/1997 | Wales et al. | |
| 5,704,534 A | 1/1998 | Huitema et al. | |
| 5,706,997 A | 1/1998 | Green et al. | |
| 5,706,998 A | 1/1998 | Plyley et al. | |
| 5,709,334 A | 1/1998 | Sorrentino et al. | |
| 5,709,680 A | 1/1998 | Yates et al. | |
| 5,711,472 A | 1/1998 | Bryan | |
| 5,713,505 A | 2/1998 | Huitema | |
| 5,715,987 A | 2/1998 | Kelley et al. | |
| 5,715,988 A | 2/1998 | Palmer | |
| 5,718,359 A | 2/1998 | Palmer et al. | |
| 5,732,871 A | 3/1998 | Clark et al. | |
| 5,735,445 A | 4/1998 | Vidal et al. | |
| 5,743,456 A | 4/1998 | Jones et al. | |
| 5,749,968 A * | 5/1998 | Melanson et al. | 118/300 |
| 5,752,644 A | 5/1998 | Bolanos et al. | |
| 5,752,965 A * | 5/1998 | Francis et al. | 606/151 |
| 5,758,814 A | 6/1998 | Gallagher et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,779,132 A | 7/1998 | Knodel et al. | |
| 5,782,396 A | 7/1998 | Mastri et al. | |
| 5,782,397 A | 7/1998 | Koukline | |
| 5,785,232 A | 7/1998 | Vidal et al. | |
| 5,794,834 A | 8/1998 | Hamblin et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,799,857 A | 9/1998 | Robertson et al. | |
| 5,820,009 A | 10/1998 | Melling et al. | |
| 5,823,066 A | 10/1998 | Huitema et al. | |
| 5,826,776 A | 10/1998 | Schulze et al. | |
| 5,829,662 A | 11/1998 | Allen et al. | |
| 5,833,690 A | 11/1998 | Yates et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,871,135 A | 2/1999 | Williamson, IV et al. | |
| 5,878,937 A | 3/1999 | Green et al. | |
| 5,878,938 A | 3/1999 | Bittner et al. | |
| 5,893,506 A | 4/1999 | Powell | |
| 5,894,979 A | 4/1999 | Powell | |
| 5,901,895 A | 5/1999 | Heaton et al. | |
| 5,911,353 A | 6/1999 | Bolanos et al. | |
| 5,915,616 A | 6/1999 | Viola et al. | |
| 5,918,791 A | 7/1999 | Sorrentino et al. | |
| 5,941,442 A | 8/1999 | Geiste et al. | |
| 5,954,259 A | 9/1999 | Viola et al. | |
| 5,988,479 A | 11/1999 | Palmer | |
| 6,007,521 A * | 12/1999 | Bidwell et al. | 604/264 |
| 6,010,054 A | 1/2000 | Johnson et al. | |
| 6,017,356 A | 1/2000 | Frederick et al. | |
| 6,022,352 A | 2/2000 | Vandewalle | |
| 6,032,849 A | 3/2000 | Mastri et al. | |
| 6,033,105 A * | 3/2000 | Barker et al. | 366/182.3 |
| 6,050,472 A | 4/2000 | Shibata | |
| 6,053,899 A * | 4/2000 | Slanda et al. | 604/500 |
| 6,079,606 A | 6/2000 | Milliman et al. | |
| 6,083,234 A | 7/2000 | Nicholas et al. | |
| 6,102,271 A | 8/2000 | Longo et al. | |
| 6,109,500 A | 8/2000 | Alli et al. | |
| 6,119,913 A | 9/2000 | Adams et al. | |
| H1904 H | 10/2000 | Yates et al. | |
| 6,126,058 A | 10/2000 | Adams et al. | |
| 6,131,789 A | 10/2000 | Schulze et al. | |
| 6,155,473 A | 12/2000 | Tompkins et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,320,123 B1 | 11/2001 | Reimers | |
| 6,330,965 B1 | 12/2001 | Milliman et al. | |
| 6,358,224 B1 | 3/2002 | Tims et al. | |
| 6,398,797 B2 * | 6/2002 | Bombard et al. | 606/153 |
| 6,416,486 B1 | 7/2002 | Wampler | |
| 6,443,973 B1 | 9/2002 | Whitman | |
| 6,488,197 B1 | 12/2002 | Whitman | |
| 6,491,201 B1 | 12/2002 | Whitman | |
| 6,505,768 B2 | 1/2003 | Whitman | |
| 6,522,101 B2 | 2/2003 | Malackowski | |
| 6,578,751 B2 | 6/2003 | Hartwick | |
| 6,601,749 B2 | 8/2003 | Sullivan et al. | |
| 6,619,529 B2 | 9/2003 | Green et al. | |
| 6,629,988 B2 | 10/2003 | Weadock | |
| 6,644,532 B2 | 11/2003 | Green et al. | |
| 6,669,073 B2 | 12/2003 | Milliman et al. | |
| 6,681,978 B2 | 1/2004 | Geiste et al. | |
| 6,681,979 B2 | 1/2004 | Whitman | |
| 6,695,199 B2 | 2/2004 | Whitman | |
| 6,698,643 B2 | 3/2004 | Whitman | |
| 6,699,214 B2 * | 3/2004 | Gellman | 604/82 |
| 6,716,233 B1 | 4/2004 | Whitman | |
| 6,755,338 B2 | 6/2004 | Hahnen et al. | |
| 6,773,438 B1 | 8/2004 | Knodel et al. | |
| 6,786,382 B1 | 9/2004 | Hoffman | |
| 6,793,652 B1 | 9/2004 | Whitman et al. | |
| 6,802,822 B1 * | 10/2004 | Dodge | 604/82 |
| 6,805,273 B2 | 10/2004 | Bilotti et al. | |
| 6,817,508 B1 | 11/2004 | Racenet et al. | |
| 6,817,509 B2 | 11/2004 | Geiste et al. | |
| 6,830,174 B2 | 12/2004 | Hillstead et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,877,647 B2 | 4/2005 | Green et al. | |
| 6,905,057 B2 | 6/2005 | Swayze et al. | |
| 6,945,444 B2 | 9/2005 | Gresham et al. | |
| 6,953,138 B2 | 10/2005 | Dworak et al. | |
| 6,953,139 B2 | 10/2005 | Milliman et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 6,988,650 B2 | 1/2006 | Schwemberger et al. | |
| 7,000,819 B2 | 2/2006 | Swayze et al. | |
| 7,008,433 B2 * | 3/2006 | Voellmicke et al. | 606/93 |
| 7,014,640 B2 * | 3/2006 | Kemppainen et al. | 606/86 R |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,730 B2 | 6/2006 | Ehrenfels et al. | |
| 7,055,731 B2 | 6/2006 | Shelton, IV et al. | |
| 7,059,508 B2 | 6/2006 | Shelton, IV et al. | |
| 7,066,944 B2 | 6/2006 | Laufer et al. | |
| 7,070,083 B2 | 7/2006 | Jankowski | |
| 7,083,075 B2 | 8/2006 | Swayze et al. | |
| 7,097,089 B2 | 8/2006 | Marczyk | |
| 7,114,642 B2 | 10/2006 | Whitman | |
| 7,128,253 B2 | 10/2006 | Mastri et al. | |
| 7,128,254 B2 | 10/2006 | Shelton, IV et al. | |
| 7,140,527 B2 | 11/2006 | Ehrenfels et al. | |
| 7,143,924 B2 | 12/2006 | Scirica et al. | |

| Patent/Pub No. | Date | Inventor(s) |
|---|---|---|
| 7,143,925 B2 | 12/2006 | Shelton, IV et al. |
| 7,143,926 B2 | 12/2006 | Shelton, IV et al. |
| 7,159,750 B2 | 1/2007 | Racenet et al. |
| 7,168,604 B2 | 1/2007 | Milliman et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,225,964 B2 | 6/2007 | Mastri et al. |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,829 B2 | 2/2008 | Arad et al. |
| 7,361,168 B2 * | 4/2008 | Makower et al. ............ 604/509 |
| 7,364,061 B2 | 4/2008 | Swayze et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,410,086 B2 | 8/2008 | Ortiz et al. |
| 7,422,136 B1 | 9/2008 | Marczyk |
| 7,424,965 B2 | 9/2008 | Racenet et al. |
| 7,431,188 B1 | 10/2008 | Marczyk |
| 7,434,715 B2 | 10/2008 | Shelton, IV et al. |
| 7,438,209 B1 | 10/2008 | Hess et al. |
| 7,441,685 B1 | 10/2008 | Boudreaux |
| 7,464,847 B2 | 12/2008 | Viola et al. |
| 7,494,039 B2 | 2/2009 | Racenet et al. |
| 7,506,790 B2 | 3/2009 | Shelton, IV |
| 2002/0032463 A1 * | 3/2002 | Cruise et al. ............... 606/214 |
| 2002/0117534 A1 | 8/2002 | Green et al. |
| 2003/0216778 A1 | 11/2003 | Weadock |
| 2004/0028502 A1 | 2/2004 | Cummins |
| 2004/0068266 A1 * | 4/2004 | Delmotte .................... 606/92 |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0111081 A1 | 6/2004 | Whitman et al. |
| 2004/0122471 A1 | 6/2004 | Toby et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0193170 A1 * | 9/2004 | Kemppainen et al. ......... 606/92 |
| 2004/0204735 A1 * | 10/2004 | Shiroff et al. ............... 606/190 |
| 2004/0222268 A1 | 11/2004 | Bilotti et al. |
| 2004/0232196 A1 | 11/2004 | Shelton, IV et al. |
| 2004/0232199 A1 | 11/2004 | Shelton, IV et al. |
| 2004/0232201 A1 | 11/2004 | Wenchell et al. |
| 2004/0243176 A1 | 12/2004 | Hahnen et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0070958 A1 | 3/2005 | Swayze et al. |
| 2005/0072827 A1 | 4/2005 | Mollenauer |
| 2005/0103819 A1 | 5/2005 | Racenet et al. |
| 2005/0107824 A1 | 5/2005 | Hillstead et al. |
| 2005/0131390 A1 | 6/2005 | Heinrich et al. |
| 2005/0145671 A1 | 7/2005 | Viola |
| 2005/0165415 A1 | 7/2005 | Wales |
| 2005/0173490 A1 | 8/2005 | Shelton, IV |
| 2005/0184121 A1 * | 8/2005 | Heinrich ................. 227/175.1 |
| 2005/0187576 A1 | 8/2005 | Whitman et al. |
| 2005/0189397 A1 | 9/2005 | Jankowski |
| 2005/0203550 A1 | 9/2005 | Laufer et al. |
| 2005/0230453 A1 | 10/2005 | Viola |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025813 A1 | 2/2006 | Shelton et al. |
| 2006/0025816 A1 | 2/2006 | Shelton |
| 2006/0049229 A1 | 3/2006 | Milliman et al. |
| 2006/0060630 A1 | 3/2006 | Shelton, IV et al. |
| 2006/0085031 A1 * | 4/2006 | Bettuchi .................... 606/215 |
| 2006/0085033 A1 * | 4/2006 | Criscuolo et al. ........... 606/219 |
| 2006/0097026 A1 | 5/2006 | Shelton |
| 2006/0100643 A1 | 5/2006 | Laufer et al. |
| 2006/0108393 A1 * | 5/2006 | Heinrich et al. .......... 227/179.1 |
| 2006/0111738 A1 * | 5/2006 | Wenchell ................... 606/186 |
| 2006/0122636 A1 | 6/2006 | Bailly et al. |
| 2006/0142772 A1 | 6/2006 | Ralph et al. |
| 2006/0151567 A1 | 7/2006 | Roy |
| 2006/0180634 A1 | 8/2006 | Shelton, IV et al. |
| 2006/0226196 A1 | 10/2006 | Hueil et al. |
| 2006/0253069 A1 * | 11/2006 | Li et al. .................... 604/93.01 |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023477 A1 | 2/2007 | Whitman et al. |
| 2007/0034666 A1 | 2/2007 | Holsten et al. |
| 2007/0034668 A1 | 2/2007 | Holsten et al. |
| 2007/0045379 A1 | 3/2007 | Shelton, IV |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |

| | | | | | | |
|---|---|---|---|---|---|---|
| 2008/0078803 A1 | 4/2008 | Shelton et al. | DE | 10314072 A1 | 12/2004 | |
| 2008/0078804 A1 | 4/2008 | Shelton et al. | EP | 0122046 A1 | 10/1984 | |
| 2008/0078805 A1 | 4/2008 | Omaits et al. | EP | 0033548 B1 | 5/1986 | |
| 2008/0078806 A1 | 4/2008 | Omaits et al. | EP | 0276104 A2 | 7/1988 | |
| 2008/0078807 A1 | 4/2008 | Hess et al. | EP | 0639349 A2 | 2/1994 | |
| 2008/0078808 A1 | 4/2008 | Hess et al. | EP | 0593920 A1 | 4/1994 | |
| 2008/0082115 A1 | 4/2008 | Morgan et al. | EP | 0600182 A2 | 6/1994 | |
| 2008/0082124 A1 | 4/2008 | Hess et al. | EP | 0630612 A1 | 12/1994 | |
| 2008/0082125 A1 | 4/2008 | Murray et al. | EP | 0634144 A1 | 1/1995 | |
| 2008/0082126 A1 | 4/2008 | Murray et al. | EP | 0646356 A2 | 4/1995 | |
| 2008/0083813 A1 | 4/2008 | Zemlok et al. | EP | 0646357 A1 | 4/1995 | |
| 2008/0164296 A1 | 7/2008 | Shelton et al. | EP | 0669104 A1 | 8/1995 | |
| 2008/0167522 A1 | 7/2008 | Giordano et al. | EP | 0679367 A2 | 11/1995 | |
| 2008/0167644 A1 | 7/2008 | Shelton et al. | EP | 0392547 B1 | 12/1995 | |
| 2008/0167670 A1 | 7/2008 | Shelton et al. | EP | 0685204 A1 | 12/1995 | |
| 2008/0167671 A1 | 7/2008 | Giordano et al. | EP | 0699418 A1 | 3/1996 | |
| 2008/0167672 A1 | 7/2008 | Giordano et al. | EP | 0702937 A1 | 3/1996 | |
| 2008/0167736 A1 | 7/2008 | Swayze et al. | EP | 0705571 A1 | 4/1996 | |
| 2008/0169327 A1 | 7/2008 | Shelton et al. | EP | 0484677 B2 | 6/1996 | |
| 2008/0169328 A1 | 7/2008 | Shelton | EP | 0541987 B1 | 7/1996 | |
| 2008/0169329 A1 | 7/2008 | Shelton et al. | EP | 0667119 B1 | 7/1996 | |
| 2008/0169330 A1 | 7/2008 | Shelton et al. | EP | 0770355 A1 | 5/1997 | |
| 2008/0169331 A1 | 7/2008 | Shelton et al. | EP | 0503662 B1 | 6/1997 | |
| 2008/0169332 A1 | 7/2008 | Shelton et al. | EP | 0625335 B1 | 11/1997 | |
| 2008/0169333 A1 | 7/2008 | Shelton et al. | EP | 0552423 B1 | 1/1998 | |
| 2008/0210738 A1 | 9/2008 | Shelton et al. | EP | 0592244 B1 | 1/1998 | |
| 2008/0237296 A1* | 10/2008 | Boudreaux et al. ....... 227/176.1 | EP | 0648476 B1 | 1/1998 | |
| 2008/0237298 A1 | 10/2008 | Schall et al. | EP | 0603472 B1 | 11/1998 | |
| 2008/0296343 A1 | 12/2008 | Schall et al. | EP | 0605351 B1 | 11/1998 | |
| 2008/0296345 A1 | 12/2008 | Shelton, IV et al. | EP | 0878169 A1 | 11/1998 | |
| 2008/0296346 A1 | 12/2008 | Shelton, IV et al. | EP | 0879742 A1 | 11/1998 | |
| 2008/0296347 A1 | 12/2008 | Shelton, IV et al. | EP | 0760230 81 | 2/1999 | |
| 2008/0300579 A1 | 12/2008 | Broehl et al. | EP | 0537572 B1 | 6/1999 | |
| 2008/0300580 A1 | 12/2008 | Shelton, IV et al. | EP | 0552050 B1 | 5/2000 | |
| 2008/0300613 A1 | 12/2008 | Shelton, IV et al. | EP | 1 086 713 B1 | 3/2001 | |
| 2008/0308601 A1 | 12/2008 | Timm et al. | EP | 1090592 A1 | 4/2001 | |
| 2008/0308602 A1 | 12/2008 | Timm et al. | EP | 1256318 B1 | 5/2001 | |
| 2008/0308603 A1 | 12/2008 | Shelton, IV et al. | EP | 0908152 B1 | 1/2002 | |
| 2008/0308604 A1 | 12/2008 | Timm et al. | EP | 0872213 B1 | 5/2002 | |
| 2008/0308606 A1 | 12/2008 | Timm et al. | EP | 1238634 A2 | 9/2002 | |
| 2008/0308607 A1 | 12/2008 | Timm et al. | EP | 0656188 B1 | 1/2003 | |
| 2008/0314954 A1 | 12/2008 | Boudreaux | EP | 0829235 B1 | 6/2003 | |
| 2008/0314955 A1 | 12/2008 | Boudreaux et al. | EP | 0813843 B1 | 10/2003 | |
| 2008/0314956 A1 | 12/2008 | Boudreaux | EP | 0741996 B1 | 2/2004 | |
| 2008/0314957 A1 | 12/2008 | Boudreaux | EP | 0705570 B1 | 4/2004 | |
| 2008/0314961 A1 | 12/2008 | Boudreaux et al. | EP | 1426012 A1 | 6/2004 | |
| 2008/0314962 A1 | 12/2008 | Boudreaux | EP | 0888749 B1 | 9/2004 | |
| 2009/0001121 A1 | 1/2009 | Hess et al. | EP | 1477119 A1 | 11/2004 | |
| 2009/0001123 A1 | 1/2009 | Morgan et al. | EP | 1479345 A1 | 11/2004 | |
| 2009/0001124 A1 | 1/2009 | Hess et al. | EP | 1479347 A1 | 11/2004 | |
| 2009/0001125 A1 | 1/2009 | Hess et al. | EP | 1479348 A1 | 11/2004 | |
| 2009/0001126 A1 | 1/2009 | Hess et al. | EP | 1520521 A1 | 4/2005 | |
| 2009/0001128 A1 | 1/2009 | Weisenburgh, II et al. | EP | 1520523 A1 | 4/2005 | |
| 2009/0001130 A1 | 1/2009 | Hess et al. | EP | 1520525 A1 | 4/2005 | |
| 2009/0005807 A1 | 1/2009 | Hess et al. | EP | 1522264 A1 | 4/2005 | |
| 2009/0005808 A1 | 1/2009 | Hess et al. | EP | 1550408 A1 | 7/2005 | |
| 2009/0005809 A1 | 1/2009 | Hess et al. | EP | 1557129 A1 | 7/2005 | |
| 2009/0012556 A1 | 1/2009 | Boudreaux et al. | EP | 1064883 B1 | 8/2005 | |
| 2009/0024085 A1* | 1/2009 | To et al. ............... 604/95.01 | EP | 1621138 A2 | 2/2006 | |
| 2009/0048583 A1* | 2/2009 | Williams et al. ......... 604/890.1 | EP | 1621141 A2 | 2/2006 | |
| 2009/0076534 A1 | 3/2009 | Shelton, IV et al. | EP | 1652481 A2 | 5/2006 | |
| | | | EP | 1382303 B1 | 6/2006 | |
| | FOREIGN PATENT DOCUMENTS | | EP | 1045672 B1 | 8/2006 | |
| | | | EP | 1617768 B1 | 8/2006 | |
| CA | 2512960 A1 | 1/2006 | EP | 1702567 A2 | 9/2006 | |
| CA | 2514274 A1 | 1/2006 | EP | 1129665 B1 | 11/2006 | |
| DE | 273689 C | 5/1914 | EP | 1256317 B1 | 12/2006 | |
| DE | 1775926 A | 1/1972 | EP | 1728473 A1 | 12/2006 | |
| DE | 9412228 U | 9/1994 | EP | 1728475 A2 | 12/2006 | |
| DE | 19924311 A1 | 11/2000 | EP | 1479346 B1 | 1/2007 | |
| DE | 69328576 T2 | 1/2001 | EP | 1484024 B1 | 1/2007 | |
| DE | 20112837 U1 | 10/2001 | EP | 1754445 A2 | 2/2007 | |
| DE | 20121753 U1 | 4/2003 | EP | 1759812 A1 | 3/2007 | |

| | | | |
|---|---|---|---|
| EP | 1300117 B1 | 8/2007 |
| EP | 1813199 A1 | 8/2007 |
| EP | 1813207 A1 | 8/2007 |
| EP | 1839596 A1 | 2/2008 |
| EP | 1897502 A1 | 3/2008 |
| EP | 1749486 B1 | 3/2009 |
| FR | 999646 A | 2/1952 |
| FR | 1112936 A | 3/1956 |
| FR | 2765794 A | 1/1999 |
| GB | 939929 A | 10/1963 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/35464 A1 | 11/1996 |
| WO | WO 97/34533 A1 | 9/1997 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094747 A1 | 11/2003 |
| WO | WO 03094743 A1 * | 11/2003 |
| WO | WO 2003094746 A1 * | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |
| WO | WO 2007/121579 A1 | 11/2007 |
| WO | WO 2007/142625 A2 | 12/2007 |
| WO | WO 2008/045383 A2 | 4/2008 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

* cited by examiner

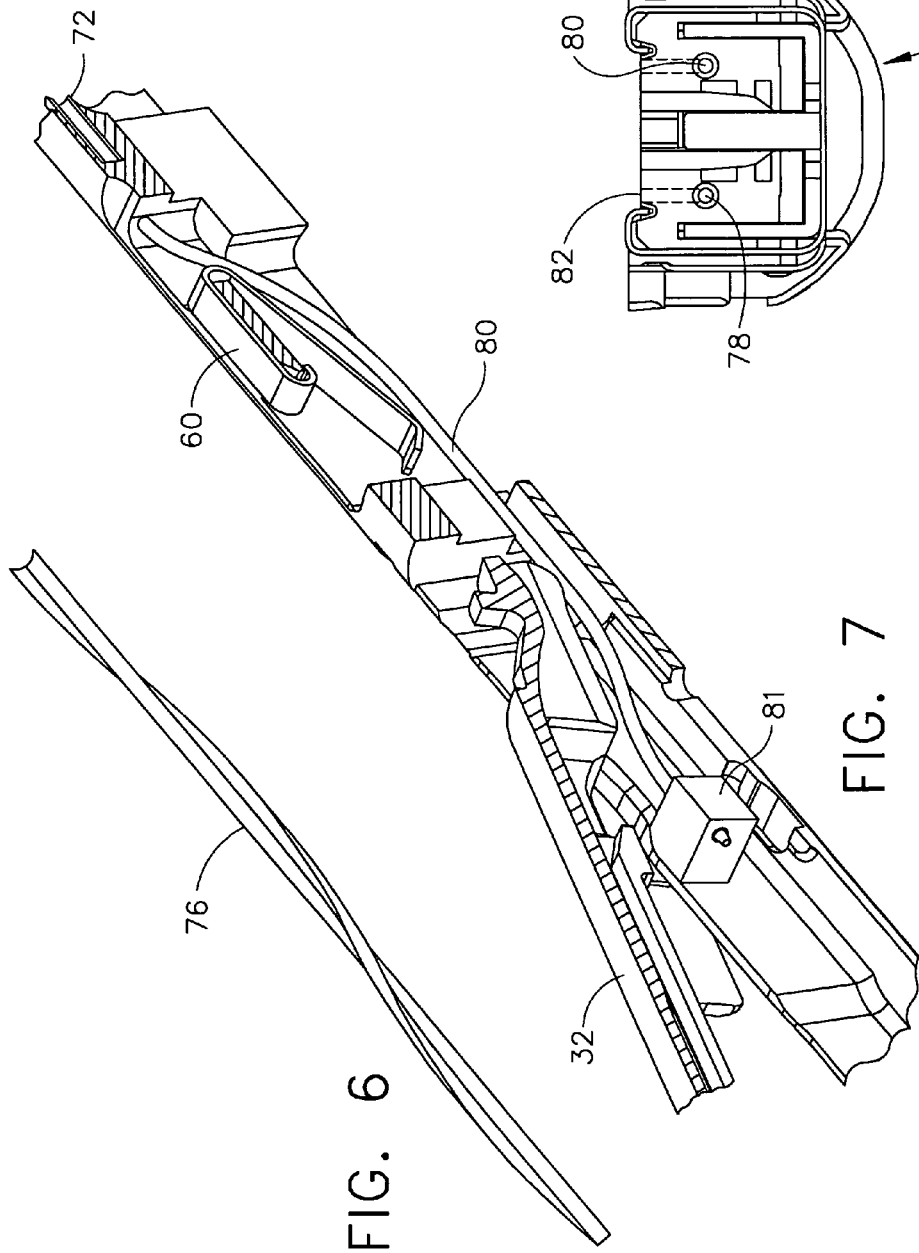

SURGICAL STAPLING INSTRUMENTS STRUCTURED FOR DELIVERY OF MEDICAL AGENTS

FIELD OF THE INVENTION

The present invention generally relates to surgical instruments. The invention more particularly relates to delivery and application of medical agents in association with the use of surgical instruments to promote closure and healing of severed and stapled tissue.

BACKGROUND

Conventional surgical staplers that can be used to simultaneously make longitudinal incisions in tissue and apply lines of staples on opposing sides of the incisions are known in the art. Such instruments commonly include a pair of cooperating jaw members that, when employed in endoscopic or laparoscopic applications, are capable of passing through a cannula passageway. One of the jaw members typically receives a staple cartridge having at least two laterally spaced rows of staples. The other jaw member defines an anvil having staple-forming pockets correspondingly aligned with the rows of staples in the cartridge. Such stapling instruments may also include a plurality of reciprocating wedges that pass through openings in the staple cartridge when driven and engage drivers supporting the staples to effect the firing of the staples toward the anvil and through tissue.

Examples of surgical staplers suitable for use with endoscopic applications are described in U.S. patent application No. US 2004/0232196 A1. In operation of the surgical stapler, a clinician closes or clamps the jaw members of the stapler on tissue to position the tissue prior to firing or activation of the stapler. Once the clinician has determined that the jaw members are clamping the tissue in a desired position, then the surgical stapler can be fired by the clinician to create an incision in the tissue and at the same time staple tissue surrounding the incision. This simultaneous action of the stapler avoids complications that often arise when the severing and stapling operations are performed sequentially (or at different times) with different surgical tools (i.e., one device is used to sever the tissue, and then another device is used to staple the tissue).

In general, application of certain medical agents to tissue incisions can promote healing, reduce the possibility of infection, and/or promote proper sealing of the incisions. If assisted by the action of such medical agents, many surgical staplers could achieve better surgical results with respect to enhanced healing, improved infection resistance, and improved sealing of tissue incisions. However, the structure of many conventional surgical staplers, and the procedures in which such staplers are employed, do not leverage the benefits of medical agents or systems that dispense medical agents.

In view of the foregoing, there is a need for improved surgical instruments and medical agent dispensing systems than can more effectively and efficiently promote closure, treatment, and healing of tissue incisions severed and stapled during operations involving surgical staplers.

SUMMARY

In accordance with the present invention, various embodiments of a medical agent dispensing system can be provided. The medical agent dispensing system may be structured for use with a surgical severing/stapling instrument structured for severing and stapling tissue. The dispensing system may include: at least one storage reservoir structured for storing at least a component of a medical agent; a gear pump casing in communication with the storage reservoir; a screw pump auger positioned within the gear pump casing capable of rotational manipulation to move the medical agent through the gear pump casing; and, at least one agent tube in communication with the gear pump casing. The agent tube may be structured for communication with a least one agent port formed in a staple cartridge of the surgical instrument for dispensing the medical agent therethrough.

In accordance with the invention, various embodiments of a surgical severing/stapling instrument including a medical agent dispensing system can be provided. The surgical instrument may include a handle portion including at least one storage reservoir structured for storing at least a component of a medical agent, and a shaft portion connected to the handle portion. The shaft portion may include a gear pump casing in communication with the storage reservoir, wherein the gear pump casing includes a screw pump auger extending therethrough capable of rotational manipulation to move the medical agent through the gear pump casing. The surgical instrument may also include an end effector portion operatively associated with the shaft portion that has a staple cartridge positioned removably therein. At least one agent tube may be provided in communication with the gear pump casing; and the agent tube may extend from the shaft portion to communicate with a least one agent port formed in the staple cartridge of the surgical instrument. The agent port may be structured to permit the medical agent to be dispensed therethrough.

BRIEF DESCRIPTION OF THE FIGURES

The accompanying drawings, which are incorporated into and constitute a part of this specification, illustrate embodiments of the invention. Together with the description of the embodiments provided herein, the drawings serve to explain the principles of the present invention for those skilled in the art.

FIG. 6 includes an enlarged, three-dimensional view of a screw pump auger that may be employed in accordance with various embodiments of the invention;

FIG. 7 includes an enlarged, partially cut-away, three-dimensional view of a portion of the instrument of FIG. 1;

FIG. 8 includes an end view of the channel of the surgical instrument of FIG. 2; and, FIG. 9 includes a process flow diagram illustrating various aspects of an example of a method for using embodiments of the medical agent dispensing system of the present invention.

DESCRIPTION

Figure 1:
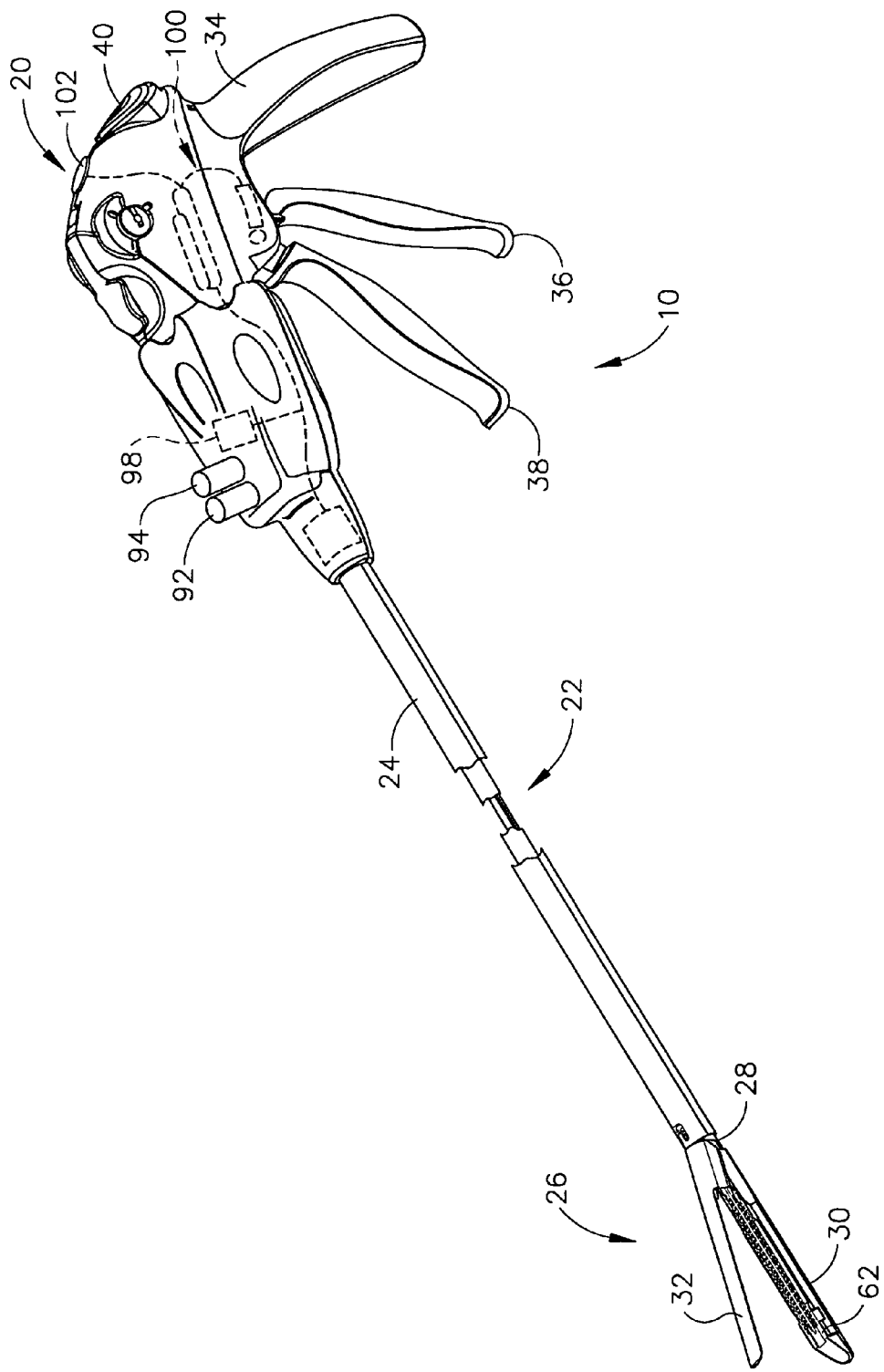
FIG. 1 depicts an three-dimensional, partially cut-away, partially schematic view of a surgical instrument that may be provided in association with embodiments of a medical agent dispensing system in accordance with the present invention.
Figure 2:
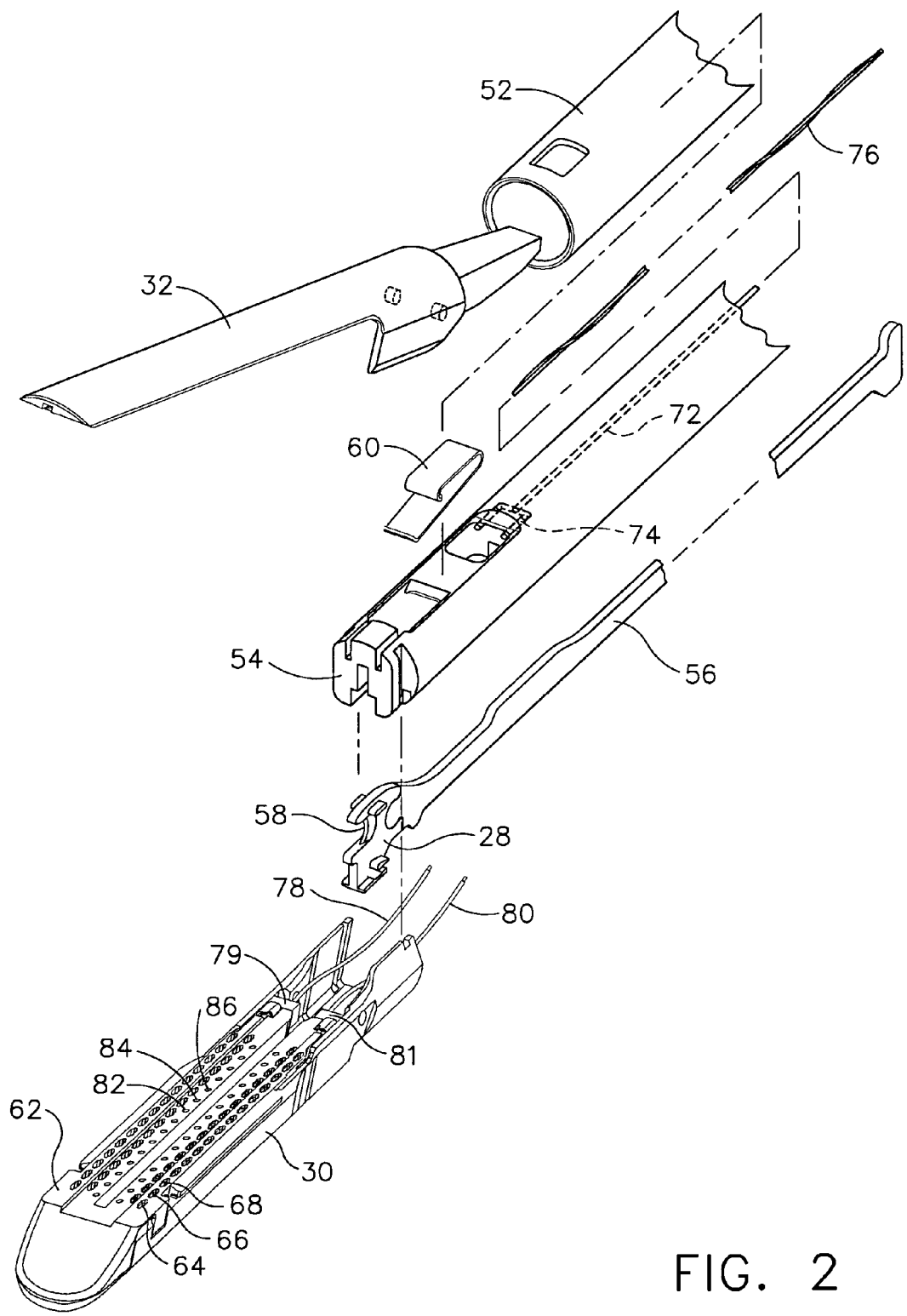
FIG. 2 illustrates a disassembled, three-dimensional view of the end effector and a shaft portion of the surgical instrument of FIG. 1.

As applied herein, the term "tissue" may include a variety of human or animal tissues, membranes, or other organic substrates. The term "tissue" may also include any substance, substrate, or composition of matter capable of being severed and stapled by the various embodiments of surgical stapling/severing instruments described herein.

As applied herein, the term "medical agent" may include a variety of chemicals, liquids, high viscosity fluids, powders or other compositions of matter that may be applied to tissues. Examples of "medical agents" include, without limitation, hemostatic agents, healing agents, adhesives, sealants, antibacterial agents, infection-resistant agents, analgesics, and various other kinds of medicinal or beneficial substances.

With general reference to the figures, and in association with various embodiments of the invention, a surgical severing/stapling instrument 10 may be structured with a handle portion 20 that is connected to an implement portion 22. The implement portion 22 may include a shaft 24 which extends distally from the handle portion 20 and terminates in an end effector 26. The end effector 26 may include an actuator or E-beam firing mechanism ("firing bar") 28 that controls spacing between an elongated channel 30 and a pivotally translatable anvil 32 included within the end effector 26. It can be seen that the spacing between the channel 30 and the anvil 32 may be configured to promote effective stapling and severing of tissue during use of the surgical instrument 10 by a clinician, for example.

The handle portion 20 of the instrument 10 may include a pistol grip 34 toward which a closure trigger 36 may be pivotally drawn by the clinician, for example, to cause clamping or closing of the anvil 32 toward the channel 30 of the end effector 26. In operation, the tissue of a patient, for example, may be clamped by the closing of the anvil 32 toward the channel 30. A firing trigger 38 positioned adjacent to the closure trigger 36 can be pivotally drawn in the direction of the pistol grip 34 to substantially simultaneously staple and sever tissue clamped in the end effector 26 of the instrument 10. In a surgical operation, the clinician first activates the closure trigger 36 to clamp the tissue of a patient, for example. Once the clinician is satisfied with the positioning of the end effector 26, the closure trigger 36 may be drawn back to a fully closed and locked position proximate to the pistol grip 34. The firing trigger 38 of the instrument 10 may then be actuated to sever and staple the clamped tissue. The firing trigger 38 may springedly return to a normal, inactivated state when the clinician removes pressure applied to the firing trigger 38. A release button 40 positioned on the proximal end of the handle portion 20 may be pressed by the clinician to release the locked closure trigger 36 to its normally open position (as shown in FIG. 1).

In various embodiments, the distal end of the shaft 24 may include a closure tube 52 structured to receive and contain portions of the components of the end effector 26, such as the anvil 32 and the channel 30. The closure tube 52 may also be structured to receive a spine 54 extending therethrough that supports a knife shaft 56 having a distally positioned severing edge 58. The knife shaft 56 may operatively interact with the firing bar 28 at the severing edge 58 of the knife shaft 56. A knife spring 60 may be inserted within the spine 54 and structured with a resilient downward bias that promotes proper and secure positioning of the knife shaft 56 within the spine 54. In operation, when the instrument 10 is fired, the knife shaft 56 and its severing edge 58 are moved through the channel 30 by a knife rod 61 to sever tissue clamped between the anvil 32 and the channel 30. The channel 30 may be structured to receive a removable staple cartridge 62 therein. The staple cartridge 62 may have multiple staple holes (such as illustratively representative staple holes 64, 66, 68) formed therein and through which multiple staples (not shown) may be driven that staple severed tissue when the instrument 10 is fired. In certain embodiments, the staple cartridge 62 may be an "ETS45" or "ETS60" six-row cartridge, for example, marketed by Ethicon Endo-Surgery, Inc., of Cincinnati, Ohio.

Examples of the structure and operation of typical surgical stapling instruments that may be provided in association with embodiments of the present invention are disclosed in a United States published patent application to Shelton et al. entitled, "Surgical Stapling Instrument having Separate Distinct Closing and Firing Systems" (U.S. Pub. No. 2004/0232196, Ser. No. 10/441,632, filed on May 20, 2003), the entirety of which is hereby incorporated by reference. A1

Figure 3:
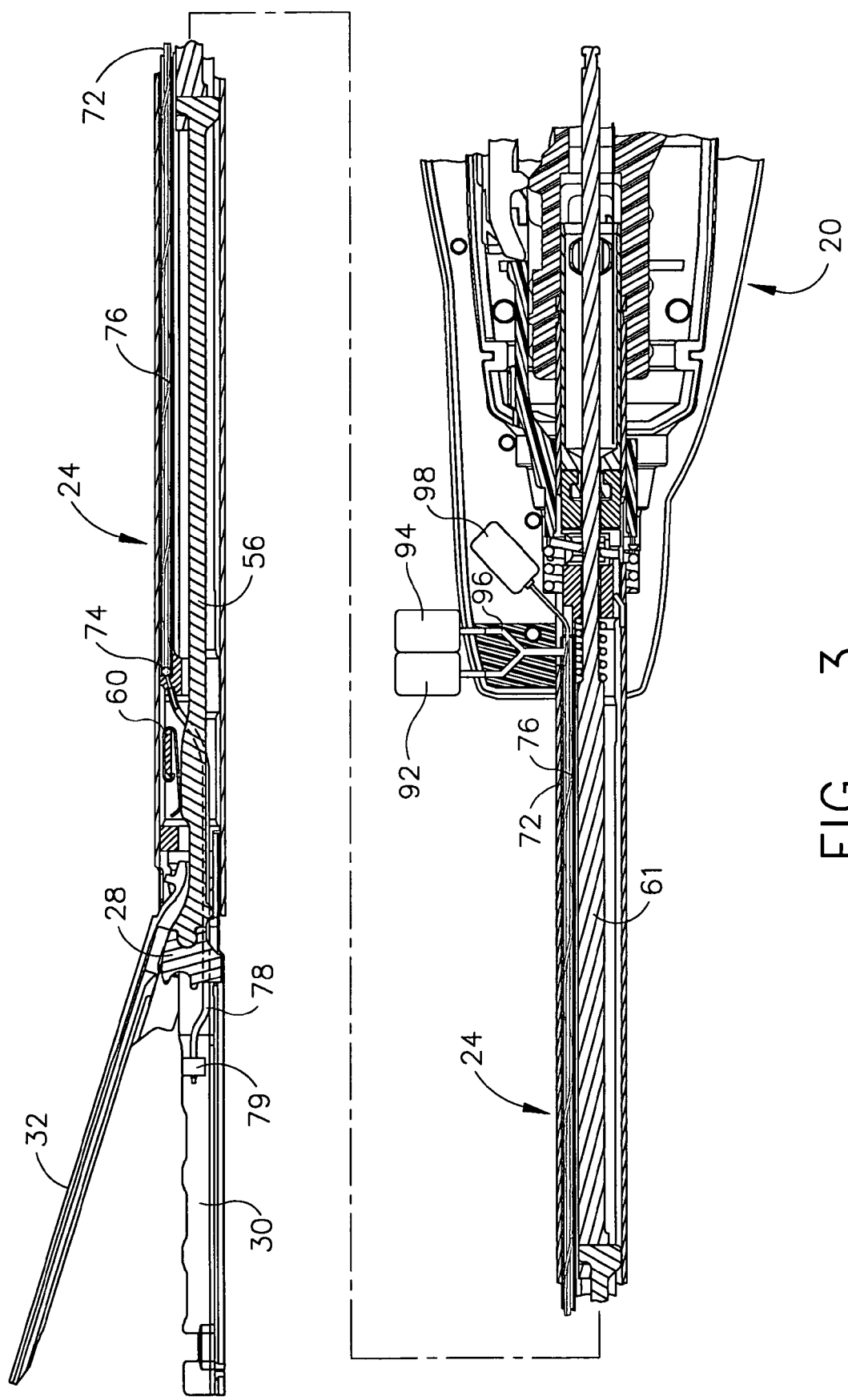
FIG. 3 includes schematic depictions of handle, shaft and end effector portions of the surgical instrument of FIG. 1.
Figure 4:
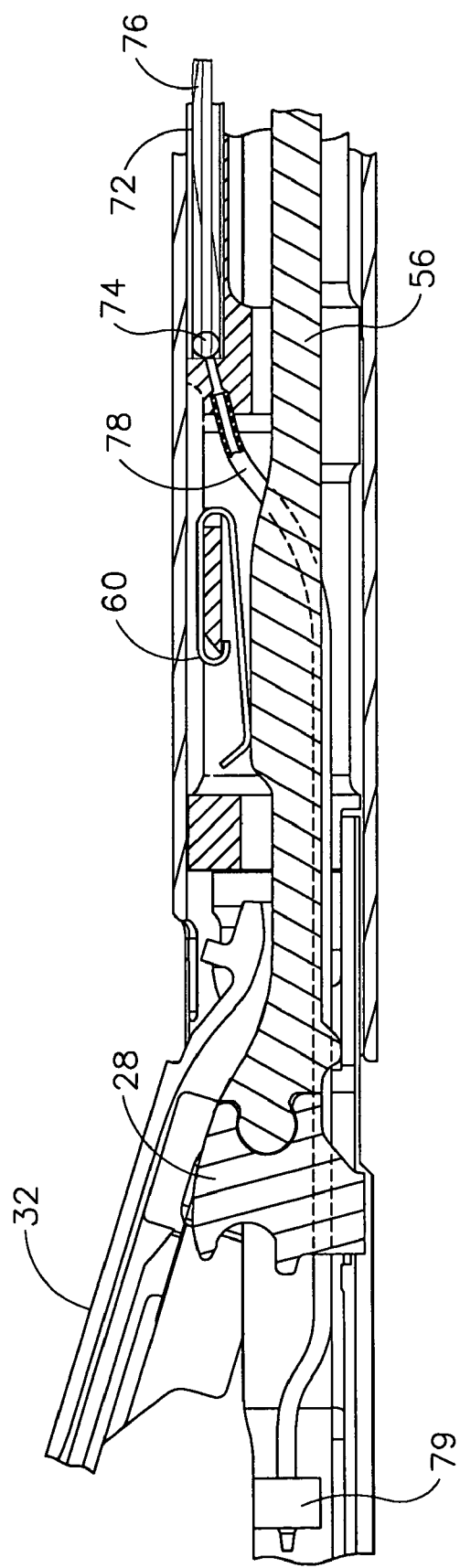
FIG. 4 includes an enlarged view of the shaft and end effector portions of the surgical instrument of FIG. 3.
Figure 5:
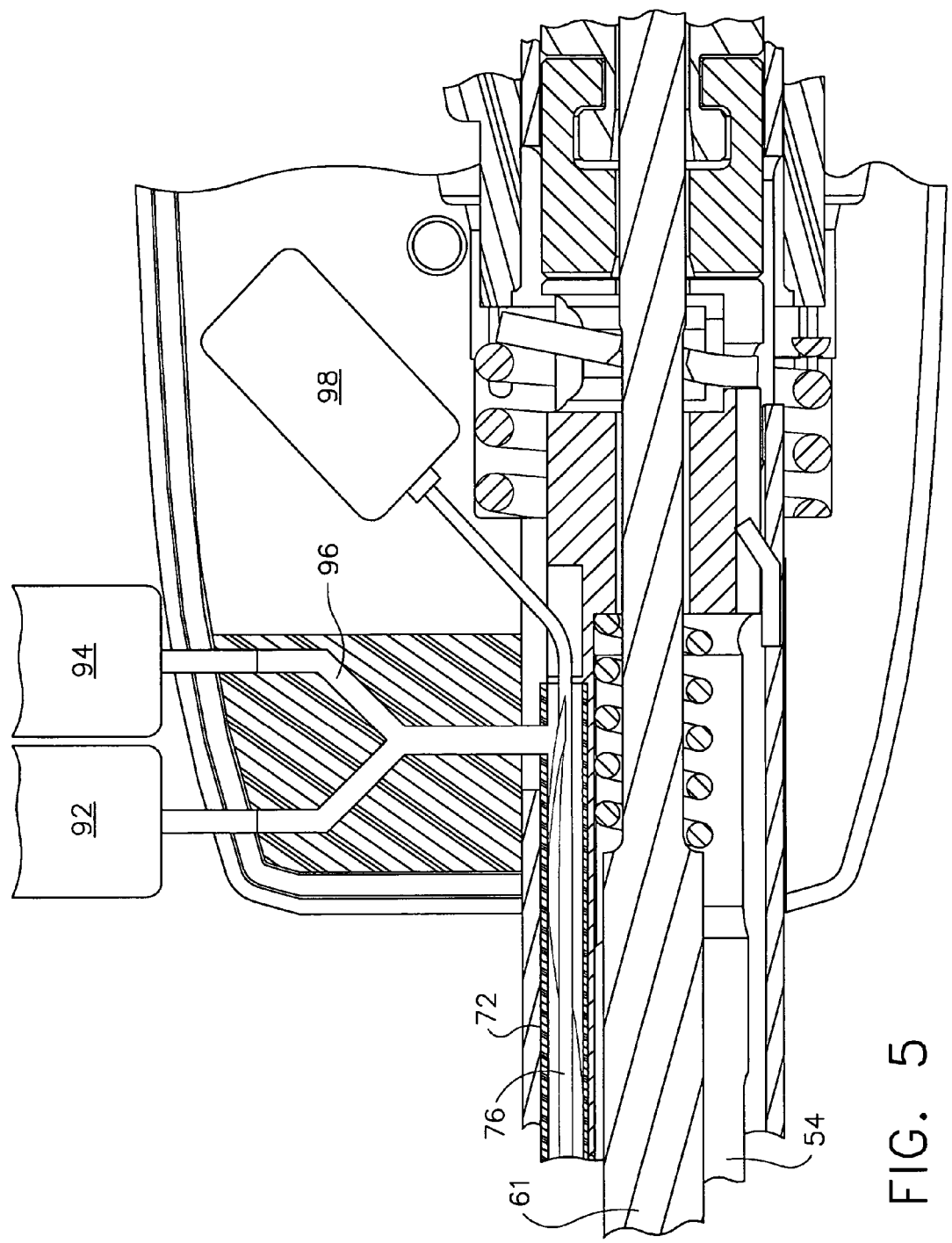
FIG. 5 includes a enlarged view of the shaft and handle portions of the surgical instrument of FIG. 3.

With regard to embodiments of a medical agent dispensing system that may be provided in conjunction with the surgical instrument 10, a gear pump casing 72 may be positioned to extend longitudinally through the spine 54, and may extend from the handle portion 20 of the instrument 10 to a lateral manifold 74. The gear pump casing 72 may be structured to receive therethrough a screw pump auger 76 that is capable of rotational manipulation when positioned within the gear pump casing 72. FIG. 6 shows an example of a screw pump auger 76 that may be used in accordance with various embodiments of the invention. One or more agent tubes 78, 80 may be positioned to communicate both with the lateral manifold 74 and with a plurality of agent ports (such as illustratively representative agent ports 82, 84, 86) formed in the staple cartridge 62 generally adjacent to the staple holes 64, 66, 68 of the cartridge 62. The agent tubes 78, 80 may be structured for communication with the agent ports 82, 84, 86 in the staple cartridge 62 as shown in the end view of the cartridge 62 of FIG. 8. While a row of agent ports 82, 84, 86 is shown positioned next to both sides of a longitudinal center line of the channel 30, it can be appreciated that more or less such agent ports 82, 84, 86 may be provided in the cartridge 62. For example, more agent ports 82, 84, 86 may be provided in place of one or more of the staple holes 64, 66, 68 formed in the cartridge 62 as shown. With particular reference to FIGS. 3 and 5, one or more structures such as mounting blocks 79, 81 may be included within the channel 30 to facilitate securement and stability of the agent tubes 78, 80 (respectively) within the instrument 10. Also, it can be seen that the agent tubes 78, 80 (such as the left-hand side agent tube 78, as shown in FIG. 4, for example) may be positioned generally adjacent to the knife shaft 56 as the agent tubes 78, 80 extend longitudinally through the shaft 24.

In various embodiments, the handle portion 20 may include one or more medical agent storage reservoirs 92, 94 mounted on the handle portion 20 and in communication with the casing 72. The storage reservoirs 92, 94 may contain a variety of medical agents, or components thereof, that can be beneficially applied to severed and stapled tissue by action of the dispensing system in connection with use of the surgical instrument 10. While multiple storage reservoirs 92, 94 are depicted with the instrument 10 for convenience of disclosure, certain embodiments of the invention may employ only a single storage reservoir or more than two storage reservoirs. It can be seen that employing multiple storage reservoirs 92, 94 can facilitate real-time mixing of multiple-component medical agents during operation of the medical agent dispensing system. For example, one storage reservoir 92 may contain a powder and the other storage reservoir 94 may contain a liquid. The powder and the liquid in the storage reservoirs 92, 94 may be mixed during operation of the instrument 10, such as by directing the substances through the Y-manifold 96 (as shown in FIGS. 3 and 5, for example). It can be appreciated that storing and deploying components of a medical agent separately may preserve the shelf life and thus the effectiveness of the individual components. In another example, the use of multiple storage reservoirs 92, 94 permits the use of two-part adhesives, for example, in connection with operation of the dispensing system within the instrument 10.

Also, in various embodiments of the medical agent dispensing system of the present invention, an electric motor 98 may be included within the handle portion 20 with a mechanical linkage structured to drive rotation of the screw pump auger 76 within the gear pump casing 72 upon activation of the motor 98. Those skilled in the art will appreciate that the electric motor 98 may be any conventional battery-driven or AC-powered motor provided with specifications (e.g., a motor rating) suitable for safe and effective use of the motor 98 in association with operation of the surgical instrument 10. In certain embodiments, the electric motor 98 may be activated through conventional electrical circuitry or components 100 that can be operatively associated with the firing trigger 38, the release button 40, and/or an independent manual activation switch 102 of the instrument 10. The electrical circuitry 100 may be configured to activate the motor 98 automatically in association with the firing operation of the instrument 10, for example; and/or to activate the motor 98 manually through use of the switch 102 which may be pressed by the clinician, for example, when using the instrument 10. In certain embodiments, a mechanically driven rotary trigger, for example, may be configured to interact with the mechanical linkage operatively associated with the casing 72 to drive rotation of the screw pump auger 76 within the casing 72.

Figure 9:
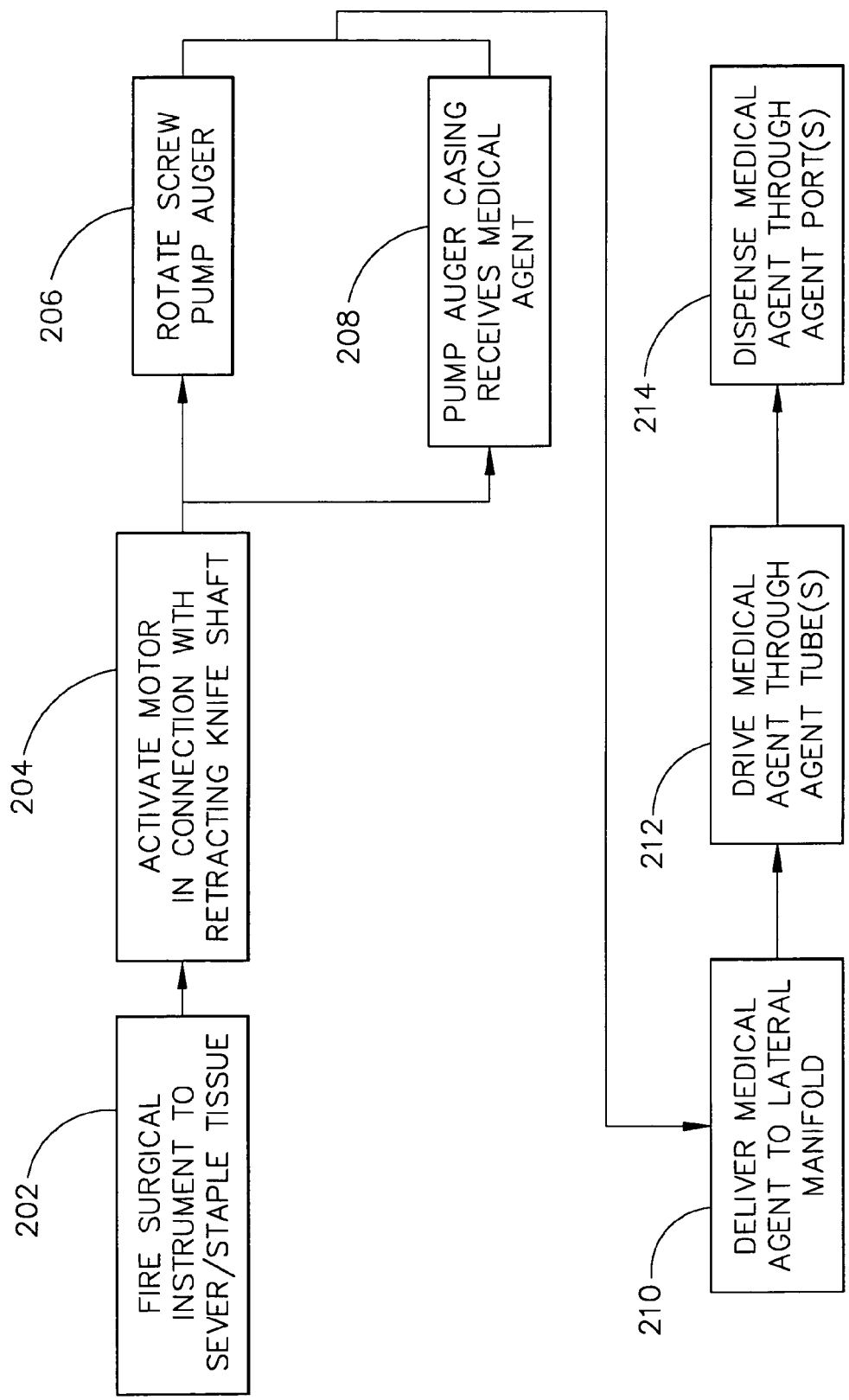

With reference to FIG. 9, a process flow diagram illustrates a method of applying the instrument 10 with the medical agent dispensing system in a surgical procedure performed on tissue, in accordance with various embodiments of the invention. At step 202, the instrument 10 may be fired as described above to sever tissue and to apply staples to areas on both sides of an incision made in the tissue. At step 204, in connection with retraction of the knife shaft 56 from the severed/stapled tissue, the electric motor 98 may be activated to initiate rotation of the screw pump auger 76 within the gear pump casing 72 at step 206. At step 208 (which may occur substantially in parallel with step 206), the gear pump casing 72 receives a quantity of a medical agent, or components combined to create a quantity of the medical agent, from the Y-manifold 96. At step 210, the medical agent is delivered by rotational action of the screw pump auger 76 to the lateral manifold 74. At step 212, the medical agent may be driven through the agent tubes 78, 80 to be dispensed at step 214 through the plurality of agent ports 82, 84, 86 in the staple cartridge 62. Once dispensed through the plurality of agent ports 82, 84, 86, the medical agent may then cover or deluge at least a portion of tissue areas severed and stapled by action of the instrument 10 at step 202.

It will be appreciated that the terms "proximal" and "distal" may be used herein as convenient terms of relative orientation, such as with reference to a clinician gripping a handle of an instrument. For example, the end effector 26 may be considered "distal" with respect to the "proximal" handle portion 20 (see, e.g., FIG. 1). It will be further appreciated that, for convenience and clarity of disclosure, spatial terms of relative orientation such as "vertical" and "horizontal" or "downward" and "upward" may be used herein with respect to the drawings. Those skilled in the art will appreciate, however, that surgical instruments may be used in many orientations and positions, and such terms are not intended to be limiting and absolute.

Any patent, publication, or other disclosure material, in whole or in part, that is said to be incorporated by reference herein is done so only to the extent that the incorporated material does not conflict with existing definitions, statements, or other disclosure material set forth in the present disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The examples presented herein are intended to illustrate potential and specific implementations of the present invention for those skilled in the art. No particular aspect or aspects of the examples included herein are necessarily intended to limit the scope of the present invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable in a typical computer system or database system. However, because such elements are well known in the art and because they do not facilitate a better understanding of the present invention, a discussion of such elements may not be provided herein.

Any element expressed herein as a means for performing a specified function is intended to encompass any way of performing that function including, for example, a combination of elements that perform that function. Furthermore the invention, as defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments of the present invention disclosed herein, a single component may be replaced by multiple components, and multiple components may be replaced by a single component, to perform a given function or functions. Except where such substitution would not be operative to practice embodiments of the present invention, such substitution is within the scope of the present invention.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that surgical instruments structured in accordance with the present invention may find use in many surgical procedures, including but not limited to laparoscopic procedures and open procedures. Moreover, the unique and novel aspects of the embodiments of the present invention may find utility when used in connection with other forms of stapling apparatuses without departing from the spirit and scope of the present invention.

What is claimed is:

1. A surgical severing/stapling instrument including a medical agent dispensing system, the instrument comprising:

a handle portion including at least one storage reservoir structured for storing at least a component of a medical agent, wherein the at least one storage reservoir is supported by the handle portion;

a shaft portion connected to the handle portion, the shaft portion including a gear pump casing in communication with the storage reservoir, the gear pump casing including a screw pump auger extending therethrough using rotational manipulation to move the medical agent through the gear pump casing;

an end effector portion operatively associated with the shaft portion, the end effector including a channel having a staple cartridge positioned removably therein, said end effector further supporting a knife bar therein, said knife bar being selectively movable from a retracted position to fired positions upon application of firing motions thereto and selectively movable from the fired positions to the retracted position upon application of a retraction motion thereto;

a firing trigger configured to apply said firing motions and said retraction motion;

at least one agent tube in communication with the gear pump casing, the agent tube extending from the shaft portion to communicate with at least one agent port formed in the staple cartridge for dispensing the medical agent therethrough, such that said screw pump auger is automatically activated to pump said medical agent from said at least one storage reservoir through said gear pump casing and said at least one agent tube upon an actuation of said firing trigger, which initiates the application of said retraction motion to said knife bar.

2. The instrument of claim 1, wherein the medical agent includes a hemostatic agent.

3. The instrument of claim 1, wherein the medical agent includes an adhesive.

4. The instrument of claim 1, wherein the gear pump casing is in communication with the agent tube through a lateral manifold.

5. The instrument of claim 1, further comprising at least a second agent tube in communication with the gear pump casing, wherein the first agent tube communicates with a first plurality of agent ports formed in the staple cartridge, and the second agent tube communicates with a second plurality of agent ports formed in the staple cartridge.

6. The instrument of claim 1, further comprising the handle portion including at least a second storage reservoir in communication with the gear pump casing, the second storage reservoir being structured for storing at least a component of the medical agent.

7. The instrument of claim 6, wherein the component stored in the first storage reservoir and the component in the second storage reservoir are designed to be combined to form the medical agent.

8. A surgical instrument comprising:

an end effector operably supporting a staple cartridge and a knife bar therein, said knife bar being selectively movable from a retracted position to fired positions upon application of firing motions thereto and selectively movable from the fired positions to the retracted position upon application of a retraction motion thereto;

at least one medical agent storage reservoir in fluid communication with at least one agent port in said staple cartridge;

a pumping member, comprising:
an electric motor;
a pump casing;
a rotatable member positioned within said pump casing; and
a mechanical linkage operably connecting said motor and said rotatable member, wherein said pumping member is configured to pump medical agent from said at least one medical agent storage reservoir through said at least one agent port upon initiation of an application of said retraction motion to said knife bar; and an actuator operably coupled with said knife bar and said motor, wherein the actuation of said actuator retracts said knife bar and operates said motor.

9. The surgical instrument of claim 8, wherein the medical agent includes a hemostatic agent.

10. The surgical instrument of claim 8, wherein the medical agent includes an adhesive.

11. The surgical instrument of claim 8 wherein said
pump casing is in communication with the storage reservoir; and wherein said rotatable member comprises a screw pump auger positioned within the pump casing, the screw pump auger using rotational manipulation to move the medical agent through the pump casing; and
at least one agent tube in communication with the pump casing, the agent tube being structured for communication with the at least one agent port in the staple cartridge.

12. The surgical instrument of claim 11 wherein the pump casing is positioned to extend longitudinally through a spine of the surgical instrument.

13. The surgical instrument of claim 11, wherein the pump casing is in communication with the agent tube through a lateral manifold.

14. The surgical instrument of claim 13, wherein the agent tube is in communication with both the lateral manifold and a plurality of the agent ports.

15. The surgical instrument of claim 11, further comprising at least a second agent tube in communication with the pump casing, wherein the first agent tube communicates with a first plurality of agent ports formed in the staple cartridge, and the second agent tube communicates with a second plurality of agent ports formed in the staple cartridge.

16. The surgical instrument of claim 8, further comprising at least one agent port being formed generally adjacent to at least one staple hole in the staple cartridge.

17. The surgical instrument of claim 11, further comprising at least a second storage reservoir in communication with the pump casing, the second storage reservoir being structured for storing at least a component of the medical agent.

18. The surgical instrument of claim 17, wherein the component stored in the first storage reservoir and the component in the second storage reservoir are designed to be combined to form the medical agent.

19. The surgical instrument of claim 11, further comprising a Y-manifold in communication with both the first storage reservoir and the second storage reservoir.

20. The surgical instrument of claim 11 wherein said pumping member is configured to pump medical agent from said at least one medical agent storage reservoir only upon commencement of an application of said retraction motion to said knife bar.

* * * * *